(12) United States Patent
Dorn et al.

(10) Patent No.: US 8,062,344 B2
(45) Date of Patent: Nov. 22, 2011

(54) VARIABLE SPEED SELF-EXPANDING STENT DELIVERY SYSTEM AND LUER LOCKING CONNECTOR

(75) Inventors: Jürgen Dorn, Neulussheim (DE); Michael Vogel, Karlsruhe (DE)

(73) Assignee: Angiomed GmbH & Co. Medizintechnik KG, Karlsruhe (DE)

( * ) Notice: Subject to any disclaimer, the term of this patent is extended or adjusted under 35 U.S.C. 154(b) by 0 days.

(21) Appl. No.: 12/640,956

(22) Filed: Dec. 17, 2009

(65) Prior Publication Data

US 2010/0094399 A1    Apr. 15, 2010

Related U.S. Application Data

(60) Division of application No. 10/824,033, filed on Apr. 14, 2004, now abandoned, which is a continuation-in-part of application No. 10/476,351, filed as application No. PCT/EP02/04727 on Apr. 29, 2002, now Pat. No. 7,550,001, said application No. 10/824,033 is a continuation-in-part of application No. 10/481,351, filed as application No. PCT/EP02/06784 on Jun. 19, 2002, now Pat. No. 7,553,322.

(30) Foreign Application Priority Data

Apr. 30, 2001 (GB) ................................. 0110551.9
Jun. 19, 2001 (GB) ................................. 0114939.2

(51) Int. Cl.
*A61F 2/06* (2006.01)

(52) U.S. Cl. ...................................... 623/1.11; 606/108

(58) Field of Classification Search .................. 606/108, 606/194, 195, 198, 192; 623/1.11, 1.12; 600/585

See application file for complete search history.

(56) References Cited

U.S. PATENT DOCUMENTS

| 1,988,060 A | 1/1935 | Vollenbroich |
| 2,934,211 A | 4/1960 | Shivek |
| 2,939,680 A | 6/1960 | Powell |
| 3,070,057 A | 12/1962 | Dezzani |
| 3,562,427 A | 2/1971 | Yano et al. |
| 3,585,707 A | 6/1971 | Stevens |
| 3,871,382 A | 3/1975 | Mann |
| 3,881,423 A | 5/1975 | Woods et al. |
| 4,256,113 A | 3/1981 | Chamness |
| 4,553,545 A | 11/1985 | Maass et al. |

(Continued)

FOREIGN PATENT DOCUMENTS

CA    2155527 A1    8/1994

(Continued)

OTHER PUBLICATIONS

Jul. 17, 2009 Non-final Office Action in U.S. Appl. No. 10/824,033, filed Apr. 14, 2004.

(Continued)

*Primary Examiner* — Victor Nguyen
(74) *Attorney, Agent, or Firm* — Rutan & Tucker, LLP

(57) ABSTRACT

A stent delivery system that includes an inner member and an outer retractable sheath is operated by a handle that permits retraction of the sheath at more than one speed. The sheath may be retracted in small, incremental steps or in a single, more rapid stroke. The stent delivery system may include releasably locking of the inner member and outer sheath in a fixed position and also may facilitate admission of liquid into the device.

4 Claims, 5 Drawing Sheets

U.S. PATENT DOCUMENTS

| | | |
|---|---|---|
| 4,580,568 A | 4/1986 | Gianturco |
| 4,616,648 A | 10/1986 | Simpson |
| 4,649,922 A | 3/1987 | Wiktor |
| 4,665,918 A | 5/1987 | Garza et al. |
| 4,723,547 A | 2/1988 | Kullas et al. |
| 4,733,665 A | 3/1988 | Palmaz |
| 4,739,762 A | 4/1988 | Palmaz |
| 4,760,622 A | 8/1988 | Rohrman |
| 4,771,773 A | 9/1988 | Kropf |
| 4,800,882 A | 1/1989 | Gianturco |
| 4,856,516 A | 8/1989 | Hillstead |
| 4,886,062 A | 12/1989 | Wiktor |
| 4,889,112 A | 12/1989 | Schachner et al. |
| 4,913,141 A | 4/1990 | Hillstead |
| 4,913,683 A | 4/1990 | Gregory |
| 4,969,458 A | 11/1990 | Wiktor |
| 4,990,151 A | 2/1991 | Wallsten |
| 5,019,090 A | 5/1991 | Pinchuk |
| 5,026,377 A | 6/1991 | Burton et al. |
| 5,045,072 A | 9/1991 | Castillo et al. |
| 5,049,128 A | 9/1991 | Duquette |
| 5,054,162 A | 10/1991 | Rogers |
| 5,102,417 A | 4/1992 | Palmaz |
| 5,104,404 A | 4/1992 | Wolff |
| 5,116,365 A | 5/1992 | Hillstead |
| 5,133,732 A | 7/1992 | Wiktor |
| 5,135,536 A | 8/1992 | Hillstead |
| 5,161,547 A | 11/1992 | Tower |
| 5,163,941 A | 11/1992 | Garth et al. |
| 5,190,552 A | 3/1993 | Kelman |
| 5,201,757 A | 4/1993 | Heyn et al. |
| 5,203,774 A | 4/1993 | Gilson et al. |
| 5,209,754 A | 5/1993 | Ahluwalia |
| 5,224,939 A | 7/1993 | Holman et al. |
| 5,228,452 A | 7/1993 | Samson |
| 5,242,423 A | 9/1993 | Goodsir et al. |
| 5,254,107 A | 10/1993 | Soltesz |
| 5,275,622 A | 1/1994 | Lazarus et al. |
| 5,279,596 A | 1/1994 | Castaneda et al. |
| 5,282,824 A | 2/1994 | Gianturco |
| 5,290,295 A | 3/1994 | Querals et al. |
| 5,290,310 A | 3/1994 | Makower et al. |
| 5,292,331 A | 3/1994 | Boneau |
| 5,312,351 A | 5/1994 | Gerrone |
| 5,312,363 A | 5/1994 | Ryan et al. |
| 5,334,147 A | 8/1994 | Johnson |
| 5,336,192 A | 8/1994 | Palestrant |
| 5,346,498 A | 9/1994 | Greelis et al. |
| 5,380,283 A | 1/1995 | Johnson |
| 5,383,892 A | 1/1995 | Cardon et al. |
| 5,387,235 A | 2/1995 | Chuter |
| 5,391,172 A | 2/1995 | Williams et al. |
| 5,411,507 A | 5/1995 | Heckele |
| 5,415,664 A | 5/1995 | Pinchuk |
| 5,417,708 A | 5/1995 | Hall et al. |
| 5,421,955 A | 6/1995 | Lau et al. |
| 5,433,723 A | 7/1995 | Lindenberg et al. |
| 5,443,477 A | 8/1995 | Marin et al. |
| 5,449,373 A | 9/1995 | Pinchasik et al. |
| 5,456,694 A | 10/1995 | Marin et al. |
| 5,456,713 A | 10/1995 | Chuter |
| 5,458,615 A | 10/1995 | Klemm et al. |
| 5,466,221 A | 11/1995 | Zadini et al. |
| 5,480,423 A | 1/1996 | Ravenscroft et al. |
| 5,507,768 A | 4/1996 | Lau et al. |
| 5,507,769 A | 4/1996 | Marin et al. |
| 5,509,900 A | 4/1996 | Kirkman |
| 5,514,154 A | 5/1996 | Lau et al. |
| 5,531,690 A | 7/1996 | Solar |
| 5,536,248 A | 7/1996 | Weaver et al. |
| 5,538,510 A | 7/1996 | Fontirroche et al. |
| 5,556,389 A | 9/1996 | Liprie |
| 5,562,726 A | 10/1996 | Chuter |
| 5,562,728 A | 10/1996 | Lazarus et al. |
| 5,569,296 A | 10/1996 | Marin et al. |
| 5,571,086 A | 11/1996 | Kaplan et al. |
| 5,571,172 A | 11/1996 | Chin |
| 5,573,530 A | 11/1996 | Fleury et al. |
| 5,578,074 A | 11/1996 | Mirigian |
| 5,591,172 A | 1/1997 | Bachmann et al. |
| 5,591,196 A | 1/1997 | Marin et al. |
| 5,601,568 A | 2/1997 | Chevillon et al. |
| 5,603,721 A | 2/1997 | Lau et al. |
| 5,603,801 A | 2/1997 | DeFriese et al. |
| 5,605,530 A | 2/1997 | Fischell et al. |
| 5,609,627 A | 3/1997 | Goicoechea et al. |
| 5,618,300 A | 4/1997 | Marin et al. |
| 5,628,755 A | 5/1997 | Heller et al. |
| 5,630,801 A | 5/1997 | Roussigne et al. |
| 5,645,076 A | 7/1997 | Yoon |
| 5,649,906 A | 7/1997 | Gory et al. |
| 5,666,970 A | 9/1997 | Smith |
| 5,669,936 A | 9/1997 | Lazarus |
| 5,672,179 A | 9/1997 | Garth et al. |
| 5,674,278 A | 10/1997 | Boneau |
| 5,681,322 A | 10/1997 | Hartigan, Jr. |
| 5,683,345 A | 11/1997 | Waksman et al. |
| 5,683,451 A | 11/1997 | Lenker et al. |
| 5,690,644 A | 11/1997 | Yurek et al. |
| 5,693,084 A | 12/1997 | Chuter |
| 5,695,498 A | 12/1997 | Tower |
| 5,695,499 A | 12/1997 | Helgerson et al. |
| 5,695,517 A | 12/1997 | Marin et al. |
| 5,697,936 A | 12/1997 | Shipko et al. |
| 5,697,949 A | 12/1997 | Giurtino et al. |
| 5,704,914 A | 1/1998 | Stocking et al. |
| 5,707,376 A | 1/1998 | Kavteladze et al. |
| 5,709,703 A | 1/1998 | Lukic et al. |
| 5,713,917 A | 2/1998 | Leonhardt et al. |
| 5,713,948 A | 2/1998 | Uflacker |
| 5,716,365 A | 2/1998 | Goicoechea et al. |
| 5,716,393 A | 2/1998 | Lindenberg et al. |
| 5,720,776 A | 2/1998 | Chuter et al. |
| 5,725,534 A | 3/1998 | Rasmussen |
| 5,728,158 A | 3/1998 | Lau et al. |
| 5,733,303 A | 3/1998 | Israel et al. |
| 5,735,893 A | 4/1998 | Lau et al. |
| 5,738,667 A | 4/1998 | Solar |
| 5,741,298 A | 4/1998 | MacLeod |
| 5,749,921 A | 5/1998 | Lenker et al. |
| 5,755,777 A | 5/1998 | Chuter |
| 5,759,186 A | 6/1998 | Bachmann et al. |
| 5,766,184 A | 6/1998 | Matsuno et al. |
| 5,769,871 A | 6/1998 | Mers Kelly et al. |
| 5,776,141 A | 7/1998 | Klein et al. |
| 5,776,142 A | 7/1998 | Gunderson |
| 5,776,161 A | 7/1998 | Globerman |
| 5,776,186 A | 7/1998 | Uflacker |
| 5,780,807 A | 7/1998 | Saunders |
| 5,782,855 A | 7/1998 | Lau et al. |
| 5,788,707 A | 8/1998 | Del Toro et al. |
| 5,795,325 A | 8/1998 | Valley et al. |
| 5,800,456 A | 9/1998 | Maeda et al. |
| 5,800,520 A | 9/1998 | Fogarty et al. |
| 5,807,327 A | 9/1998 | Green et al. |
| 5,810,768 A | 9/1998 | Lopez |
| 5,810,837 A | 9/1998 | Hofmann et al. |
| 5,810,869 A | 9/1998 | Kaplan et al. |
| 5,810,872 A | 9/1998 | Kanesaka et al. |
| 5,814,062 A | 9/1998 | Sepetka et al. |
| 5,824,058 A | 10/1998 | Ravenscroft et al. |
| 5,833,694 A | 11/1998 | Poncet |
| 5,840,064 A | 11/1998 | Liprie |
| 5,843,088 A | 12/1998 | Barra et al. |
| 5,843,092 A | 12/1998 | Heller et al. |
| 5,843,120 A | 12/1998 | Israel et al. |
| 5,843,244 A | 12/1998 | Pelton et al. |
| 5,851,210 A | 12/1998 | Torossian |
| 5,860,998 A | 1/1999 | Robinson et al. |
| RE36,104 E | 2/1999 | Solar |
| 5,868,755 A | 2/1999 | Kanner et al. |
| 5,873,906 A | 2/1999 | Lau et al. |
| 5,879,382 A | 3/1999 | Boneau |
| 5,891,154 A | 4/1999 | Loeffler |
| 5,906,579 A | 5/1999 | Vander Salm et al. |
| 5,906,619 A | 5/1999 | Olson et al. |
| 5,913,897 A | 6/1999 | Corso, Jr. et al. |

| | | | | | | | |
|---|---|---|---|---|---|---|---|
| 5,919,225 | A | 7/1999 | Lau et al. | 6,319,262 | B1 | 11/2001 | Bates et al. |
| 5,925,061 | A | 7/1999 | Ogi et al. | 6,332,403 | B1 | 12/2001 | Weise et al. |
| 5,928,246 | A | 7/1999 | Gordon et al. | 6,342,067 | B1 | 1/2002 | Mathis et al. |
| 5,931,842 | A | 8/1999 | Goldsteen et al. | 6,344,053 | B1 | 2/2002 | Boneau |
| 5,944,727 | A | 8/1999 | Ahari et al. | 6,348,065 | B1 | 2/2002 | Brown et al. |
| 5,951,585 | A | 9/1999 | Cathcart et al. | 6,358,274 | B1 | 3/2002 | Thompson |
| 5,961,536 | A | 10/1999 | Mickley et al. | 6,375,676 | B1 | 4/2002 | Cox |
| 5,968,052 | A * | 10/1999 | Sullivan et al. ............... 623/1.11 | 6,383,211 | B1 | 5/2002 | Staehle |
| 5,968,053 | A | 10/1999 | Revelas | 6,391,050 | B1 | 5/2002 | Broome |
| 5,968,068 | A | 10/1999 | Dehdashtian et al. | 6,391,051 | B2 | 5/2002 | Sullivan, III et al. |
| 5,968,069 | A | 10/1999 | Dusbabek et al. | 6,395,020 | B1 | 5/2002 | Ley et al. |
| 5,972,018 | A | 10/1999 | Israel et al. | 6,402,760 | B1 | 6/2002 | Fedida |
| 5,980,515 | A | 11/1999 | Tu | 6,413,269 | B1 | 7/2002 | Bui et al. |
| 5,984,225 | A | 11/1999 | Enzinna | 6,443,979 | B1 | 9/2002 | Stalker et al. |
| 5,992,000 | A | 11/1999 | Humphrey et al. | 6,443,982 | B1 | 9/2002 | Israel et al. |
| 5,997,562 | A | 12/1999 | Zadno-Azizi et al. | 6,461,381 | B1 | 10/2002 | Israel et al. |
| 6,004,328 | A | 12/1999 | Solar | 6,488,703 | B1 | 12/2002 | Kveen et al. |
| 6,015,429 | A | 1/2000 | Lau et al. | 6,500,248 | B1 | 12/2002 | Hayashi |
| 6,019,778 | A | 2/2000 | Wilson et al. | 6,514,261 | B1 | 2/2003 | Randall et al. |
| 6,027,509 | A | 2/2000 | Schatz et al. | 6,517,569 | B2 | 2/2003 | Mikus et al. |
| 6,039,744 | A | 3/2000 | Forber | 6,520,983 | B1 | 2/2003 | Colgan et al. |
| 6,039,749 | A | 3/2000 | Marin et al. | 6,527,779 | B1 | 3/2003 | Rourke |
| 6,042,597 | A | 3/2000 | Kveen et al. | 6,572,643 | B1 | 6/2003 | Gharibadeh |
| 6,045,536 | A | 4/2000 | Meier et al. | 6,599,296 | B1 | 7/2003 | Gillick et al. |
| 6,071,263 | A | 6/2000 | Kirkman | 6,613,014 | B1 | 9/2003 | Chi |
| 6,071,286 | A | 6/2000 | Mawad | 6,613,075 | B1 | 9/2003 | Healy et al. |
| 6,077,295 | A | 6/2000 | Limon et al. | 6,629,981 | B2 | 10/2003 | Bui et al. |
| 6,080,140 | A | 6/2000 | Swaminathan et al. | 6,645,238 | B2 | 11/2003 | Smith |
| 6,083,194 | A | 7/2000 | Lopez | 6,652,506 | B2 | 11/2003 | Bowe et al. |
| 6,090,035 | A | 7/2000 | Campbell et al. | 6,660,031 | B2 * | 12/2003 | Tran et al. .................... 623/1.12 |
| 6,090,063 | A | 7/2000 | Makower et al. | 6,660,827 | B2 | 12/2003 | Lentz et al. |
| 6,090,128 | A | 7/2000 | Douglas | 6,663,666 | B1 | 12/2003 | Quiachon et al. |
| 6,096,009 | A | 8/2000 | Windheuser et al. | 6,695,862 | B2 | 2/2004 | Cox et al. |
| 6,096,045 | A | 8/2000 | Del Toro et al. | 6,716,190 | B1 | 4/2004 | Glines et al. |
| 6,096,056 | A | 8/2000 | Brown | 6,716,238 | B2 | 4/2004 | Elliott |
| 6,102,942 | A | 8/2000 | Ahari | 6,749,627 | B2 | 6/2004 | Thompson et al. |
| 6,110,191 | A | 8/2000 | Dehdashtian et al. | 6,755,854 | B2 | 6/2004 | Gillick et al. |
| 6,113,607 | A | 9/2000 | Lau et al. | 6,773,446 | B1 | 8/2004 | Dwyer et al. |
| 6,117,140 | A | 9/2000 | Munsinger | 6,786,918 | B1 | 9/2004 | Krivoruchko et al. |
| 6,117,165 | A | 9/2000 | Becker | 6,821,292 | B2 | 11/2004 | Pazienza et al. |
| 6,117,167 | A | 9/2000 | Goicoechea et al. | 6,866,669 | B2 | 3/2005 | Buzzard et al. |
| 6,123,723 | A | 9/2000 | Konya et al. | 6,884,259 | B2 | 4/2005 | Tran et al. |
| 6,129,755 | A | 10/2000 | Mathis et al. | 6,911,039 | B2 | 6/2005 | Shiu et al. |
| 6,136,007 | A | 10/2000 | Goldsteen et al. | 6,913,613 | B2 | 7/2005 | Schwarz et al. |
| 6,136,572 | A | 10/2000 | Benatti et al. | 6,939,352 | B2 * | 9/2005 | Buzzard et al. ............... 606/108 |
| 6,143,014 | A | 11/2000 | Dehdashtian et al. | 6,939,370 | B2 | 9/2005 | Hartley et al. |
| 6,143,021 | A | 11/2000 | Staehle | 7,033,368 | B2 | 4/2006 | Rourke |
| 6,146,415 | A | 11/2000 | Fitz | 7,052,511 | B2 | 5/2006 | Weldon et al. |
| 6,149,680 | A | 11/2000 | Shelso et al. | 7,122,050 | B2 | 10/2006 | Randall et al. |
| 6,156,053 | A | 12/2000 | Gandhi et al. | 7,172,617 | B2 | 2/2007 | Colgan et al. |
| 6,156,054 | A | 12/2000 | Zadno-Azizi et al. | 7,294,135 | B2 | 11/2007 | Stephens et al. |
| 6,156,063 | A | 12/2000 | Douglas | 7,323,006 | B2 | 1/2008 | Andreas et al. |
| 6,159,228 | A | 12/2000 | Frid et al. | 7,381,216 | B2 | 6/2008 | Buzzard et al. |
| 6,159,239 | A | 12/2000 | Greenhalgh | D576,725 | S | 9/2008 | Shumer et al. |
| 6,167,315 | A | 12/2000 | Coe et al. | D578,216 | S | 10/2008 | Dorn et al. |
| 6,168,610 | B1 | 1/2001 | Marin et al. | D578,643 | S | 10/2008 | Shumer et al. |
| 6,168,617 | B1 | 1/2001 | Blaeser et al. | D578,644 | S | 10/2008 | Shumer et al. |
| 6,174,327 | B1 | 1/2001 | Mertens et al. | D578,645 | S | 10/2008 | Shumer et al. |
| 6,183,509 | B1 | 2/2001 | Dibie | 7,506,650 | B2 | 3/2009 | Lowe et al. |
| 6,190,360 | B1 | 2/2001 | Iancea et al. | 7,550,001 | B2 | 6/2009 | Dorn et al. |
| 6,190,393 | B1 | 2/2001 | Bevier et al. | 7,553,322 | B2 | 6/2009 | Dorn et al. |
| 6,190,406 | B1 | 2/2001 | Duerig et al. | D598,543 | S | 8/2009 | Vogel et al. |
| 6,203,550 | B1 | 3/2001 | Olson | 7,582,054 | B2 | 9/2009 | Okada |
| 6,203,558 | B1 | 3/2001 | Dusbabek et al. | 2001/0007082 | A1 | 7/2001 | Dusbabek et al. |
| 6,210,422 | B1 | 4/2001 | Douglas | 2001/0044621 | A1 | 11/2001 | Klumb et al. |
| 6,217,585 | B1 | 4/2001 | Houser et al. | 2001/0051822 | A1 | 12/2001 | Stack et al. |
| 6,224,608 | B1 | 5/2001 | Ciccolella et al. | 2002/0004663 | A1 | 1/2002 | Gittings et al. |
| 6,238,402 | B1 | 5/2001 | Sullivan, III et al. | 2002/0035394 | A1 | 3/2002 | Fierens et al. |
| 6,238,415 | B1 | 5/2001 | Sepetka et al. | 2002/0116044 | A1 | 8/2002 | Cottone et al. |
| 6,241,692 | B1 | 6/2001 | Tu et al. | 2002/0151955 | A1 | 10/2002 | Tran et al. |
| 6,245,100 | B1 | 6/2001 | Davila et al. | 2002/0183827 | A1 | 12/2002 | Derus et al. |
| 6,248,122 | B1 | 6/2001 | Klumb et al. | 2002/0188341 | A1 | 12/2002 | Elliott |
| 6,251,132 | B1 | 6/2001 | Ravenscroft et al. | 2003/0028236 | A1 | 2/2003 | Gillick et al. |
| 6,254,608 | B1 | 7/2001 | Solar | 2003/0049295 | A1 | 3/2003 | Guggenbichler et al. |
| 6,264,689 | B1 | 7/2001 | Colgan et al. | 2003/0050686 | A1 | 3/2003 | Raeder-Devens et al. |
| 6,270,521 | B1 | 8/2001 | Fischell et al. | 2003/0074045 | A1 | 4/2003 | Buzzard et al. |
| 6,273,895 | B1 | 8/2001 | Pinchuk et al. | 2003/0163085 | A1 | 8/2003 | Tanner et al. |
| 6,287,322 | B1 | 9/2001 | Zhu et al. | 2003/0167060 | A1 | 9/2003 | Buzzard et al. |
| 6,312,407 | B1 | 11/2001 | Zadno-Azizi et al. | 2003/0191516 | A1 | 10/2003 | Weldon et al. |

| | | | | | | |
|---|---|---|---|---|---|---|
| 2004/0006380 | A1 | 1/2004 | Buck et al. | EP | 0518838 A1 | 12/1992 |
| 2004/0098079 | A1 | 5/2004 | Hartley et al. | EP | 0564894 A1 | 10/1993 |
| 2004/0098083 | A1 | 5/2004 | Tran et al. | EP | 0611556 A1 | 8/1994 |
| 2004/0143160 | A1 | 7/2004 | Couvillon | EP | 0630657 A1 | 12/1994 |
| 2004/0148009 | A1 | 7/2004 | Buzzard et al. | EP | 0633756 B1 | 1/1995 |
| 2004/0153137 | A1 | 8/2004 | Gaschino et al. | EP | 0688545 A1 | 12/1995 |
| 2004/0181239 | A1 | 9/2004 | Dorn et al. | EP | 0699451 A2 | 3/1996 |
| 2004/0193180 | A1 | 9/2004 | Buzzard et al. | EP | 0712614 A1 | 5/1996 |
| 2004/0193283 | A1 | 9/2004 | Rioux et al. | EP | 0744930 A1 | 12/1996 |
| 2004/0199240 | A1 | 10/2004 | Dorn | EP | 0747021 A2 | 12/1996 |
| 2005/0004515 | A1 | 1/2005 | Hart et al. | EP | 0752896 B1 | 1/1997 |
| 2005/0021123 | A1 | 1/2005 | Dorn et al. | EP | 0790041 A2 | 8/1997 |
| 2005/0027306 | A1 | 2/2005 | Krivoruchko et al. | EP | 0792627 A2 | 9/1997 |
| 2005/0027345 | A1 | 2/2005 | Horan et al. | EP | 0873733 A1 | 10/1998 |
| 2005/0033402 | A1 | 2/2005 | Cully et al. | EP | 0876804 A1 | 11/1998 |
| 2005/0060016 | A1 | 3/2005 | Wu et al. | EP | 0947212 A2 | 10/1999 |
| 2005/0080476 | A1 | 4/2005 | Gunderson et al. | EP | 1025813 A2 | 8/2000 |
| 2005/0085851 | A1 | 4/2005 | Fiehler et al. | EP | 1078611 A1 | 2/2001 |
| 2005/0090890 | A1 | 4/2005 | Wu et al. | EP | 1095634 A2 | 5/2001 |
| 2005/0149159 | A1 | 7/2005 | Andreas et al. | EP | 1117341 A1 | 7/2001 |
| 2005/0182475 | A1 | 8/2005 | Jen et al. | EP | 1132058 A1 | 9/2001 |
| 2005/0209670 | A1 | 9/2005 | George et al. | EP | 1155664 A2 | 11/2001 |
| 2005/0209672 | A1 | 9/2005 | George et al. | EP | 1181906 A2 | 2/2002 |
| 2005/0209674 | A1 | 9/2005 | Kutscher et al. | EP | 1199051 A2 | 4/2002 |
| 2005/0240254 | A1 | 10/2005 | Austin | EP | 1290989 A2 | 3/2003 |
| 2005/0256562 | A1 | 11/2005 | Clerc et al. | EP | 1299050 B1 | 4/2003 |
| 2005/0273151 | A1 | 12/2005 | Fulkerson et al. | EP | 1302178 A2 | 4/2003 |
| 2005/0288764 | A1 | 12/2005 | Snow et al. | EP | 1383446 A1 | 1/2004 |
| 2006/0058866 | A1 | 3/2006 | Cully et al. | EP | 1440671 A2 | 7/2004 |
| 2006/0074477 | A1 | 4/2006 | Berthiaume et al. | EP | 1447057 A1 | 8/2004 |
| 2006/0085057 | A1 | 4/2006 | George et al. | EP | 1447058 A1 | 8/2004 |
| 2006/0100686 | A1 | 5/2006 | Bolduc et al. | EP | 1637092 A2 | 3/2006 |
| 2006/0167467 | A1 | 7/2006 | Rourke | FR | 2760351 A1 | 9/1998 |
| 2006/0259124 | A1 | 11/2006 | Matsuoka et al. | FR | 2797761 A1 | 3/2001 |
| 2006/0276873 | A1 | 12/2006 | Sato | FR | 2797781 A1 | 3/2001 |
| 2007/0016164 | A1 | 1/2007 | Dudney et al. | WO | WO-9521593 A1 | 8/1995 |
| 2007/0050006 | A1 | 3/2007 | Lavelle | WO | WO-9526775 A1 | 10/1995 |
| 2007/0055339 | A1 | 3/2007 | George et al. | WO | WO-9618359 A1 | 6/1996 |
| 2007/0055342 | A1 | 3/2007 | Wu et al. | WO | WO-9811646 A1 | 3/1998 |
| 2007/0060999 | A1 | 3/2007 | Randall et al. | WO | WO-9820811 A1 | 5/1998 |
| 2007/0073379 | A1 | 3/2007 | Chang | WO | WO-9823241 A2 | 6/1998 |
| 2007/0073389 | A1 | 3/2007 | Bolduc et al. | WO | WO-9830173 A1 | 7/1998 |
| 2007/0088421 | A1 | 4/2007 | Loewen | WO | WO-9852496 A1 | 11/1998 |
| 2007/0100420 | A1 | 5/2007 | Kavanagh et al. | WO | WO-9904728 A1 | 2/1999 |
| 2007/0100422 | A1 | 5/2007 | Shumer et al. | WO | WO-9925280 A1 | 5/1999 |
| 2007/0100429 | A1 | 5/2007 | Wu et al. | WO | WO-9944541 A1 | 9/1999 |
| 2007/0112409 | A1 | 5/2007 | Wu et al. | WO | WO-9947075 A1 | 9/1999 |
| 2007/0118201 | A1 | 5/2007 | Pappas et al. | WO | WO-9951167 A2 | 10/1999 |
| 2007/0118206 | A1 | 5/2007 | Colgan et al. | WO | WO-0000104 A1 | 1/2000 |
| 2007/0168014 | A1 | 7/2007 | Jimenez et al. | WO | WO-0002503 A1 | 1/2000 |
| 2007/0191864 | A1 | 8/2007 | Shumer | WO | WO-0016718 A1 | 3/2000 |
| 2007/0191865 | A1 | 8/2007 | Pappas | WO | WO-0018330 A1 | 4/2000 |
| 2007/0191925 | A1 | 8/2007 | Dorn | WO | WO-0071059 A1 | 11/2000 |
| 2007/0194483 | A1 | 8/2007 | Guggenbichler et al. | WO | WO-0078246 A2 | 12/2000 |
| 2007/0233222 | A1 | 10/2007 | Roeder et al. | WO | WO-0078248 A1 | 12/2000 |
| 2007/0244540 | A1 | 10/2007 | Pryor | WO | WO-0132102 | 5/2001 |
| 2007/0255390 | A1 | 11/2007 | Ducke et al. | WO | WO-0134061 A1 | 5/2001 |
| 2009/0024133 | A1 | 1/2009 | Keady et al. | WO | WO-0147436 A2 | 7/2001 |
| 2009/0099638 | A1 | 4/2009 | Grewe | WO | WO-0158387 A1 | 8/2001 |
| 2010/0004606 | A1 | 1/2010 | Hansen et al. | WO | WO-0189421 A2 | 11/2001 |
| 2010/0036472 | A1 | 2/2010 | Papp | WO | WO-0203888 A2 | 1/2002 |
| 2010/0168756 | A1 | 7/2010 | Dorn et al. | WO | WO-0203889 A2 | 1/2002 |
| 2010/0174290 | A1 | 7/2010 | Wuebbeling et al. | WO | WO-02066094 A2 | 8/2002 |
| | | | | WO | WO-02083036 A2 | 10/2002 |
| FOREIGN PATENT DOCUMENTS | | | | WO | WO-02087470 A1 | 11/2002 |
| | | | | WO | WO-02102279 A2 | 12/2002 |
| DE | 02544371 A1 | 4/1976 | | WO | WO-03002020 A1 | 1/2003 |
| DE | 3132323 A1 | 4/1983 | | WO | 03061724 A2 | 7/2003 |
| DE | 4420142 A1 | 12/1995 | | WO | WO-2005004515 A1 | 1/2005 |
| DE | 29516712 U1 | 12/1995 | | WO | WO-2005039448 A1 | 5/2005 |
| DE | 19539449 A1 | 4/1997 | | WO | WO-2005053574 A2 | 6/2005 |
| DE | 29717110 U1 | 11/1997 | | WO | 2005062980 A2 | 7/2005 |
| DE | 29816878 U1 | 12/1998 | | WO | 2005065200 A2 | 7/2005 |
| DE | 29522101 | 12/1999 | | WO | 2005117759 A2 | 12/2005 |
| DE | 19921530 | 6/2000 | | WO | WO-2006104143 A1 | 10/2006 |
| DE | 19901530 A1 | 7/2000 | | WO | 2007002713 A2 | 1/2007 |
| DE | 19936059 A1 | 2/2001 | | WO | 2007005799 A1 | 1/2007 |
| DE | 20000659 U1 | 5/2001 | | WO | 2007022395 A1 | 2/2007 |
| DE | 69521346 | 4/2002 | | WO | 2007029242 A1 | 3/2007 |
| EP | 0436303 A1 | 7/1991 | | | | |

| WO | WO-2007044929 A1 | 4/2007 |
| WO | WO-2007083470 A1 | 7/2007 |
| WO | WO-2008034793 A1 | 3/2008 |

OTHER PUBLICATIONS

Nov. 30, 2007 International Search Report in international application No. PCT/EP2007/058205 filed on Aug. 7, 2007.
Nov. 30, 2007 Written Opinion of the International Searching Authority in international application No. PCT/EP2007/058205 filed on Aug. 7, 2007.
Aug. 4, 2008 International Preliminary Report on Patentability in international application No. PCT/EP2007/058205 filed on Aug. 7, 2007.
Nov. 4, 2008 International Search Report in international application No. PCT/EP2008/059040 filed on Jul. 10, 2008.
Nov. 4, 2008 Written Opinion of the ISA in international application No. PCT/EP2008/059040 filed on Jul. 10, 2008.
Sep. 29, 2009 International Preliminary Report on Patentability in international application No. PCT/EP2008/059040 filed on Jul. 10, 2008.
Dec. 15, 2005 International Search Report in international application No. PCT/US2005/019860 filed on Jun. 6, 2005.
Dec. 15, 2005 Written Opinion of the international searching authority in international application No. PCT/US2005/019860 filed on Jun. 6, 2005.
Dec. 4, 2006 International Preliminary Report on Patentability in international application No. PCT/US2005/019860 filed on Jun. 6, 2005.
Apr. 27, 2007 Written Opinion of the ISA in international application No. PCTUS2007000834 filed on Jan. 12, 2007.
Jul. 15, 2008 International Preliminary Report on Patentability in international application No. PCTUS2007000834 filed on Jan. 12, 2007.
Jan. 19, 2007 International Search Report in international application No. PCT/US2006/032228 filed on Aug. 16, 2006.
Jan. 19, 2007 Written Opinion of the ISA in international application No. PCT/US2006/032228 filed on Aug. 16, 2006.
Feb. 20, 2008 International Preliminary Report on Patentability in international application No. PCT/US2006/032228 filed on Aug. 16, 2006.
Apr. 27, 2007 International Search Report in international application No. PCT/US2007/000834 filed on Jan. 12, 2007.
"Medtronic Announces FDA Clearance of Bridge SE Biliary Stent." Business Wire, Oct 15, 2001. www.medtronic.com/newsroom/news_20011015a.html.
"Summary for the Bridge SE Biliary Self-Expanding Stent Delivery System" Jan. 14, 2002 FDA Section 510 (k) review.
Jul. 10, 2002 International Search Report in international application No. PCT/EP2002/04727 filed on Apr. 29, 2002.
Jan. 7, 2003 International Preliminary Examination Report in international application No. PCT/EP2002/04727 filed on Apr. 29, 2002.
Aug. 31, 2009 Non-Final Office Action in U.S. Appl. No. 11/505,185, filed Aug. 16, 2006.
Nov. 12, 2008 Non-Final Office Action in U.S. Appl. No. 11/652,737, filed Jan. 12, 2007.
May 27, 2009 Final Office Action in U.S. Appl. No. 11/652,737, filed Jan. 12, 2007.
Oct. 27, 2009 Non-Final Office Action in U.S. Appl. No. 11/652,737, filed Jan. 12, 2007.
Apr. 4, 2008 Non-Final Office Action in U.S. Appl. No. 10/476,351, filed May 7, 2004.
Oct. 21, 2008 Final Office Action in U.S. Appl. No. 10/476,351, filed May 7, 2004.
Feb. 4, 2009 Final Office Action in U.S. Appl. No. 10/476,351, filed May 7, 2004.
Jan. 21, 2004 International Search Report in international application No. PCT/EP2002/06784 filed on Jun. 19, 2002.
Apr. 14, 2004 International Preliminary Examination Report in international application No. PCT/EP2002/06784 filed on Jun. 19, 2002.
Bridge SE Binary System, Oct. 2002, 3 pages, http:/www.medtronicave/com/includes/content/phsycians/bridges/htm.
EP 10001359.8 filed Aug. 16, 2006 European Search Report dated May 28, 2010.
U.S. Appl. No. 10/476,351, filed May 7, 2004 Notice of Allowance dated Mar. 12, 2009.
U.S. Appl. No. 11/144,513, filed Jun. 3, 2005 Advisory Action dated Oct. 5, 2010.
U.S. Appl. No. 11/144,513, filed Jun. 3, 2005 Final Office Action dated Jul. 13, 2010.
U.S. Appl. No. 11/144,513, filed Jun. 3, 2005 Final Office Action dated Oct. 15, 2008.
U.S. Appl. No. 11/144,513, filed Jun. 3, 2005 Final Office Action dated Oct. 20, 2009.
U.S. Appl. No. 11/144,513, filed Jun. 3, 2005 Non-Final Office Action dated Feb. 2, 2010.
U.S. Appl. No. 11/144,513, filed Jun. 3, 2005 Non-Final Office Action dated Feb. 5, 2008.
U.S. Appl. No. 11/144,513, filed Jun. 3, 2005 Non-Final Office Action dated Feb. 26, 2009.
U.S. Appl. No. 11/505,185, filed Aug. 16, 2006 Non-Final Office Action dated Mar. 31, 2010.
U.S. Appl. No. 11/505,185, filed Aug. 16, 2006 Non-Final Office Action dated Oct. 7. 2010.
U.S. Appl. No. 11/652,737, filed Jan. 12, 2007 Advisory Action dated Aug. 27, 2010.
U.S. Appl. No. 11/652,737, filed Jan. 12, 2007 Final Office Action dated Jun. 10, 2010.

* cited by examiner

VARIABLE SPEED SELF-EXPANDING STENT DELIVERY SYSTEM AND LUER LOCKING CONNECTOR

PRIORITY

This application is a divisional application of U.S. patent application Ser. No. 10/824,033, filed Apr. 14, 2004, which is a continuation-in-part of: 1) U.S. patent application Ser. No. 10/476,351, now U.S. Pat. No. 7,550,001, which is a U.S. national stage application under 35 USC §371 of International Application No. PCT/EP02/04727, filed Apr. 29, 2002, which claims priority to U.K. Application No. GB 0110551.9, filed Apr. 30, 2001; and 2) U.S. patent application Ser. No. 10/481,351, now U.S. Pat. No. 7,553,322, which is a U.S. national stage application under 35 USC §371 of International Application No. PCT/EP02/06784, filed Jun. 19, 2002, which claims priority to U.K. Application No. GB 0114939.2, filed Jun. 19, 2001. Each of the foregoing applications is incorporated by reference in its entirety into this application.

FIELD OF THE INVENTION

This invention relates to stent delivery systems.

BACKGROUND

The deployment of stents at a stenting site within a human or animal body requires careful handling of the stent delivery system to be used for deploying the stent. Exact positioning of the stent at the site of the stenosis prior to and during deployment is essential. The accuracy with which the stent can be deployed with respect to the occlusion inside the body lumen, as well as the skills of the surgeon in controlling the stent delivery system, will having an impact on the outcome of the operation.

Normally, a guidewire is used, to advance a stent delivery system containing the stent to be deployed into the body to the site of the stenosis. Once the distal end of the delivery system has reached the stenting site and the stent to be released is correctly located, the stent is released. To deploy a self-expanding stent it is known to gradually withdraw an outer sheath (otherwise called sleeve) holding the stent in a radially compressed configuration and thereby allow the stent to radially expand and to anchor itself inside the body lumen. In commercially available delivery systems, the stent is prevented by an inner catheter from moving proximally with the sleeve as it retreats proximally, and is held in a radially compressed state by a co-axially disposed outer sheath or sleeve enclosing the stent and the inner catheter. The relative axial positions of the inner catheter and the outer sleeve are varied by manipulation of the delivery system.

Since the stent as well as the stenosis are not directly visible to the surgeon performing the operation, the stent deployment procedure requires a visualization procedure, usually the injection of a radiopaque fluid, in order to visualize the location of the stent inside the body lumen. The fluid is injected into an annular cavity between the inner catheter and the outer sheath. The position of the stent as well as the location of the stenosis itself can then be monitored from outside the patient's body by using X-ray imaging machines showing the images of radiopaque marker rings on the distal end of the delivery system and a reduced intensity image corresponding to the constricted volume of radiopaque fluid through the occluded site. This allows the surgeon/radiologist to find the location of the stenosis and place the stent with sufficient accuracy.

During the course of the delivery procedure, the radially compressed stent is held axially at a fixed position by a pusher surface of the inner catheter, which typically abuts the proximal end of the stent inside the outer sheath of the delivery system. The proximal movement of the outer sheath to release the stent exerts a proximally directed force onto the stent which urges the stent to move in the same way. The surgeon has to counteract this tendency of the stent to move proximally by applying an adequate, distally-directed force onto the pusher element in order to off-set the opposing forces and to thereby keep the position of the stent fixed.

Typically, the stent is mounted into the delivery system at a manufacturing site. Then, the entire assembly is sterilized and air-tightly packed in a specially designed sealed enclosure. During sterilization and packaging, there is always the risk that the co-axial components of the assembly might move so that the outer sheath may be displaced with respect to the inner catheter. Consequently, the position of the stent might be changed during these steps prior to its placement.

Therefore, it would be desirable to have a delivery system with a fluid injection port which is protected against inadvertent or premature movement of the outer sheath relative to the stent but is still simple to use and economical to manufacture.

Some delivery devices are particularly applicable to the release into the body of a self-expanding stent, such as one made from nickel-titanium shape memory alloy. Self-expanding stents usually have a basically cylindrical form prior to deployment and it is conventional to deploy these stents with a system having two components. One of these components is a sleeve or sheath which surrounds the stent and constrains it to a radially compact disposition. The other component is a so-called "pusher" which is located inside the constraining sleeve and bears against a surface of the stent. Deployment of the stent is then accomplished by proximal withdrawal of the sleeve relative to the pusher. The pusher maintains the stent in a location relative to the target site of surgery. The proximal withdrawal of the sleeve progressively releases the stent, first at its distal end and then progressively proximally along the length of the stent until, when the distal end of the sleeve is proximal of the proximal end of the stent cylinder, the stent is fully deployed. At this point, the sleeve and pusher delivery system can be withdrawn proximally out of the body, leaving the stent, expanded, in the desired location. An early disclosure of such a system can be found in Gianturco U.S. Pat. No. 4,580,568.

Radiopaque markers on the stent delivery system (sometimes supplemented by markers on the stent itself) are used to enable radiologists to visualize the location of the stent in the body. Furthermore, the stent delivery system is used as a conduit for filling the bodily lumen to be stented with radiopaque fluid, to enable the radiologist to pinpoint the location of the stenosis or other surgical site where the stent is to be placed. It is then the task of the medical practitioner performing the stenting procedure to bring the radiopaque stent markers into the desired relationship with the site of surgery as indicated by the radiopaque fluid.

There continue to be difficulties for medical practitioners in placing the stent exactly as required. What has been needed now for many years is a delivery system which a medical practitioner can manipulate manually with enough precision to bring the stent reliably into the desired location relative to the surgical site. It will be appreciated that stent delivery systems are commonly of a length around 130 cm—such as when delivered by a Seldinger technique—so the medical practitioner is to some extent handicapped by having to work at considerable distance from the stent itself.

Stents come in many different lengths. However, for all but the shortest stent length, there are, to the knowledge of the present inventor, two phases in any self-expanding stent deployment sequence.

In a first phase, initial proximal withdrawal of the surrounding sleeve releases the distal end of the stent so that this part of the stent length begins to make contact with the bodily lumen which defines the site of surgery. This first phase is characterized in that the stent is still bound to the delivery system and not to the bodily lumen. However, at the end of the first phase, enough of the length of the stent has expanded into contact with the lumen wall to fix the position of the stent relative to the lumen wall. At this point, the stent is bound to both the delivery system and the bodily lumen wall, so that any axial movement of the delivery system relative to the bodily lumen is liable to cause injury to the lumen wall.

The second phase of stent deployment is what follows thereafter, namely, the remainder of the proximal movement of the sheath to release the remaining length of the stent into the bodily lumen. It will be appreciated that any axial stress on the deployed portion of the length of the stent during deployment will transmit to axial stress on that part of the bodily lumen which is in binding engagement with the stent, with the consequence that lumen wall supported by the stent remains in tension and under stress after the stent has been fully deployed. This unwanted axial stress in the bodily tissue could be severely deleterious to the patient in one way or another and is normally to be avoided.

There are proposals in the patent literature for placement of self-expanding stents by progressive distal advancement of a surrounding sheath, to release the stent, proximal end first, terminating at the distal end of the stent. It will be appreciated that this is possible because the radial expansion of the stent opens up a lumen big enough for proximal withdrawal of the sheath from a position distal of the expanded stent. The discussion of axial stresses can be applied, mutatis mutandis, to these configurations proposed in the patent literature, in which the proximal end of the stent is deployed first.

Also previously proposed are combinations of constraining sheaths which withdraw from the stent simultaneously proximally and distally, from a starting point intermediate the ends of the stent, in order to deploy the stent first from a mid part of its length, and terminating with deployment of both the proximal and distal ends of the stent. Even in such systems, the concerns about axial stresses still apply.

For a disclosure within the state of the art of a system which distinguishes between the initial phase of stent deployment and the subsequent phase in which the remainder of the length is deployed, reference is made to WO 99/04728. In this disclosure, it is proposed to use a stent delivery system which is characterized by an initial mechanical advantage for the initial stages of stent deployment, which is large enough to overcome static frictional forces between the stent and the surrounding sheath and to allow the initial part of the length of the stent to be deployed slowly and precisely. Once the sheath has begun sliding over the stent length, and an end of the stent has expanded to engage the surrounding luminal wall, a different and lower mechanical advantage is activated, to withdraw the sheath proximally at a rate more rapid than that characteristic of the initial phase of stent deployment.

It is the experience of the present inventor that individual medical practitioners have developed their own preferred techniques for precise deployment of stents. Looking at the proximal end of the stent delivery system, with the actuator which the practitioner actually handles during the stent deployment procedure, the state of the art offers various configurations and the individual practitioners select from these possibilities the actuators which fit their particular manual skills best.

WO 99/04728, mentioned above, offers the practitioner a knurled rotary actuation element whereas WO 00/18330, DE-A-44 20142 and WO 98/23241 are examples of pistol grip devices in which deployment is accomplished by a form of squeeze handle or trigger. See EP-A-747 021 and U.S. Pat. No. 5,433,723 for other examples of rotary stent release devices.

Another approach to the accomplishment of a controlled release of a self-expanding stent can be found in U.S. Pat. No. 5,683,451, the approach relying on so-called runners which lie between the stent and a surrounding sheath. At the proximal end of the delivery system, a follower receives a hub at the proximal end of the surrounding sheath and rotation of a handle causes rotation of a threaded shaft, along which the follower advances, to carry the proximal hub of the sheath in a proximal direction to release the stent.

SUMMARY OF THE INVENTION

One aspect of this invention relates to a device for releasing into the body from a delivery system a medical prosthesis mounted on the delivery system and held by a constraint in a constrained delivery disposition. The device comprises a first abutment for the delivery system, a second abutment for an elongate element to connect the device to the prosthesis constraint, a track for the second abutment to advance along, from a starting point corresponding to constraint of the prosthesis, to a finishing point corresponding to separation of the prosthesis and constraint, and ratchet means to advance the second abutment progressively, from the starting point to the finishing point, in a plurality of actuation strokes.

According to one aspect of the present invention there is provided a device for releasing into the body from a delivery system a medical prosthesis mounted on the delivery system, of the form discussed above, and characterized by a full stroke actuator, to advance the second abutment all the way from an intermediate point on said track to said finishing point in one single stroke of the said actuator, the intermediate point being selectable by the user within a portion of the track which extends over at least half the length of the track.

In short, what the present inventor has found is that a release device which embodies both a ratchet means and a full stroke actuator is one which allows a range of individual medical practitioners, all of whom have their own preferred techniques for precise stent deployment, to practice their skilled techniques in the way that suits them best, to lay down an initial part of the length of a stent in a precise location in a bodily lumen, and then to complete the deployment of the length of the stent in a way which is so accurately and precisely controlled that the practitioner can satisfactorily avoid imposing unacceptable axial stresses on the tissue being stented.

In presently preferred embodiment, the device of the invention is realized in a device which offers the medical practitioner a trigger for successive pumping to withdraw the stent-surrounding sheath proximally stepwise, together with a slider which allows the operator to withdraw the sleeve in one stroke. Thus, the trigger provides the ratchet means of the invention and the slider provides the full stroke actuator of the invention. The inventor envisages that it will be convenient for many practitioners to utilize the trigger during the first phase of stent deployment and then, when satisfied that the stent is placed within the bodily lumen as desired, switch from the trigger to the slider in order to deploy the remaining length of the stent with as much fingertip sensitivity as possible, thereby to minimize the imposition of unwanted stresses on the bodily tissue.

Accordingly, in another aspect of the invention, there is provided a method for releasing into the body from a delivery system a medical prosthesis mounted on the delivery system and held by a constraint in a constrained delivery system, the method comprising a first release phase characterized by stepwise release of a first portion of the prosthesis, by successive actuation strokes of a ratchet means, followed by a second phase of release of the prosthesis, characterized by a single stroke of a full stroke prosthesis release actuator.

The presently preferred embodiment of the invention features a connection between the trigger and the slider which is collapsible, to allow the slider to approach the trigger from any position along its sliding length, without the need to actuate the trigger at any point during withdrawal of the stent sheath. This is conveniently accomplished by the provision of a collapsible line having one end connected to the shaft of a windlass, and the other end pulling on the sheath, the windlass reeling in the line, this reeling in being accomplished by successive passes of a toothed ratchet segment over the toothed circumference of a windlass drive gear, each pass being achieved by a squeeze of the trigger. Conveniently, the end of the line is connected to the slider. If the slider itself is gripped by the medical practitioner, and urged towards the windlass shaft, the line can collapse as the slider approaches the windlass.

This invention relates to a connector portion useful particularly, but not exclusively, as part of a device for passing fluid into an annular cavity between an inner elongate body and an outer elongate tubular body of a stent delivery system, and also relates to a stent delivery system making use of the same connector. In particular, but not exclusively, this invention relates to a connector which comprises the male portion of a luer connector. Furthermore, it relates to a device having a housing with a distal end, a proximal end and an off-axis end, wherein the housing provides a seating at the distal end thereof for the proximal end of an outer elongate tubular body which extends distally from the housing along an axis of the housing extending between the proximal and the distal ends, and wherein the distal and off-axis ends define respective openings which are in fluid communication with each other, and wherein the proximal end has a lumen which enables an inner elongate body co-axially within the outer tubular body to extend from the housing both distally and proximally along the axis thereof. It relates as well to a stent delivery system using the above-mentioned connector and device.

Another aspect of the invention relates to a stent delivery system such as that described above and that enables the surgeon both to lock the position of the inner catheter with respect to the outer sleeve and to inject fluid into the annular cavity between the inner catheter and the outer sleeve.

This object has been achieved by a simplified delivery system using the same component both for locking the position of the inner catheter with respect to the outer sleeve and for injecting fluid such as radiopaque fluid into the cavity between the inner catheter and the outer sleeve.

BRIEF DESCRIPTION OF THE DRAWINGS

The accompanying figures, referred to herein and constituting a part hereof, illustrate preferred embodiments of the present invention, and together with the description serve to explain the principles of the invention.

DETAILED DESCRIPTION OF ILLUSTRATIVE EMBODIMENTS

Figure 1:
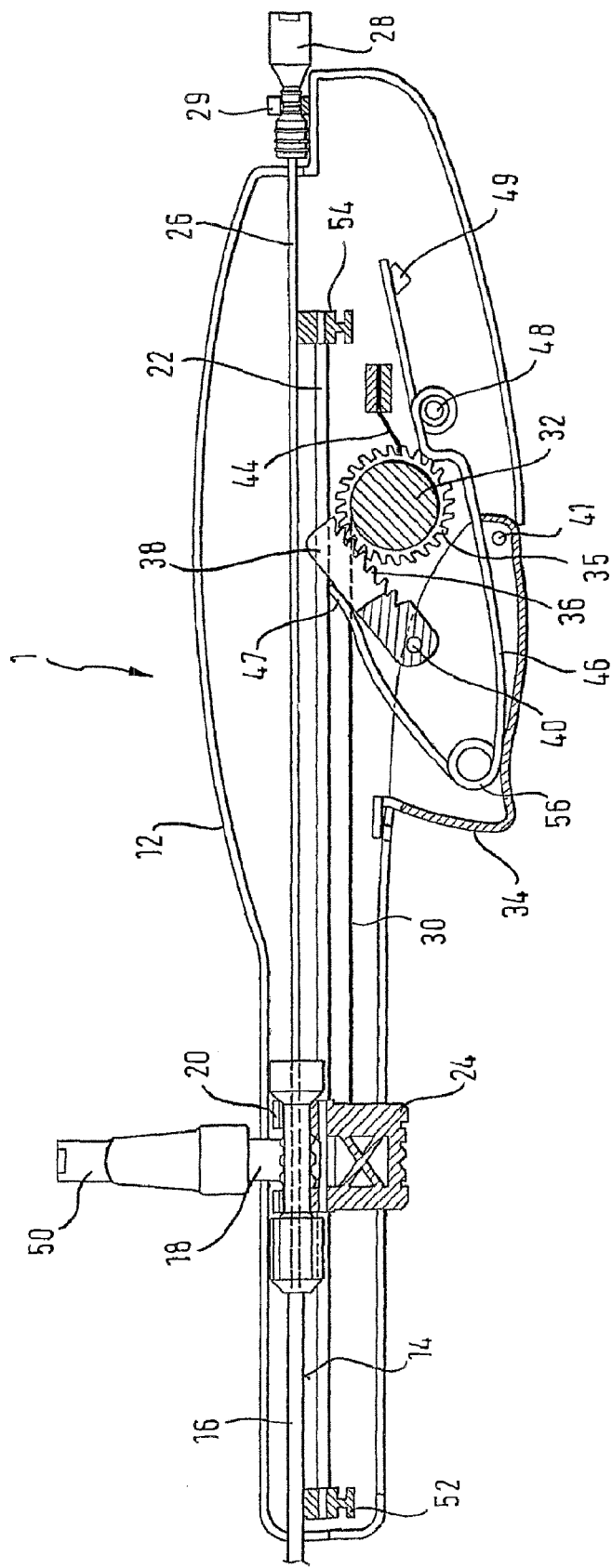
FIG. 1 is a longitudinal mid-section through a hand-held device in accordance with the present invention.

The drawings are of a preferred embodiment of the invention and FIG. 1 shows one half 12 of a molded housing of which the other half lies above the plane of the drawing.

The two housing halves define, in an assembled state, a track 14 in which can be laid the proximal end of a co-axial stent delivery device having an outer tube 16. Track 14 is formed by mating axial recesses in the two housing halves, resulting in a semi-circular channel open to the upper end in FIG. 1 of the housing.

The proximal end of the outer tube 16 carries a hub 18 which is received within a yoke 20 of a slider 24 which itself runs on a pair of rails 22. The rails 22 are not integral molded parts of the housing and are held in place by advancing a first one of the rails through a hole (not show in FIG. 1) and through fixing part 52 and feed hole in slider 24 at the distal end of the housing and into blind hole at fixing point 54 distal from the proximal end of the housing. The distal end of the rail is then bonded to the housing or fixing part 52 using an ultrasonic fusion technique. The two housing halves are then assembled and the other one of the rails is fed through another hole in the distal end of the other housing half, inserted through a feed hole in the slider 24 and pushed into another blind hole at fixing point 54. The distal end of the second rail is also bonded to the housing an ultrasonic fusion technique. Instead of ultrasonically bonding the distal ends of the rails 22 to the housing, they may equally well be adhesively bonded thereto. Although not shown in FIG. 1, rails 22 may also be an integral part of the housing 12. The length of the rails 22 may extend along the entire length of the housing 12, but is at least equal the axial length of the stent to be deployed.

The present inventors also contemplate to provide markers on the rails, provided the housing is made of a transparent material, and on the slider to indicate the length of proximal withdrawal of the outer tube 16 with respect to the position of the stent. If, for example, a marker on the slider 24 lines up with a proximal-most marker provided on one of the rails 22, this gives the medical practitioner an indication that the stent has been fully released. The slider 24 protrudes to the outside of the housing 12 at the lower end thereof in FIG. 1, enabling a person to manually urge the slider 24 along the length of the rails 22, when appropriate. The protrusion length of the slider 24 may conveniently be sufficient to be grasped by the thumb and the index finger for optimum handling of the slider.

The inner element 26 of the co-axial delivery device is a rod, or hypo-tube, or like element which extends proximally along the track 14 to a proximal hub 28 which is captivated within the proximal end of the housing 12 and so cannot move proximally or distally once the co-axial delivery device is set within the track 14. Since the opposite end of the rod 26, that is, its distal end, is normally defining the proximal end of the stent to be delivered, the length of the rod 26 defines the distance separating the proximal end of the housing 12, where the hub 28 is captivated, and the proximal end of the stent being delivered. Hub 28 is clipped into engagement with the housing at fixing point 29. Other ways of attaching hub 28 to the proximal end of housing 12 are contemplated and are obvious to those skilled in the art, such as a yoke.

The body 12 contains actuating elements to draw the slider 24 in a controlled way from the distal end of the rails 22 towards their proximal ends. This proximal sliding movement draws hub 18 proximally, and so draws outer tube 16 of the delivery device proximally. Such a movement would be useful, for example, to release a self-expanding stent from within the distal portion of the tube 16.

To effect a controlled proximal movement of the slider 24, a collapsible line in the form of a pull wire 30 runs from the slider 24 to a windlass or take-up reel shaft 32 which is adjacent a trigger 34 mounted to the housing 12. The reel shaft 32 carries a toothed gear 35, and the teeth engage with complementary teeth 36 on an elongate ratchet element 38 itself pivotably mounted at an axis 40 to the trigger 34. The trigger 34 is mounted in a recess within the housing 12 and is held in place as soon as the two housing halves are assembled.

Trigger 34 is biased to a rest position as shown in FIG. 1 by a leaf spring 46 which is pivotally mounted to the housing 12 at a mounting pin 48. One end 47 of the leaf spring 48 cooperates with the elongate ratchet means 38 and is movable thereon. The other end, beyond mounting point 48 bears against support 49 and is free to move thereon. Between the pivot 48 and the distal end of leaf spring 46 making contact with the ratchet element 38, the wire used for the leaf spring is turned into a helical spring 56. The helical spring serves for optimizing the spring-characteristic forces bearing on the ratchet element 38. From portion 56 which establishes the helical spring, the leaf spring essentially follows the contour of the interior of the trigger until another helically turned portion follows, wrapping around the mounting pin 48. At this point, the leaf spring is pivotally mounted to the housing. Thus, when pushing the trigger 34 upwards, the support 49 resists pressure from one end of the spring 46, while the other end of leaf spring 46 making contact with ratchet element 38 is free to follow the movement of the trigger 34. Subsequent to actuation of the trigger, leaf spring reaction on support 49 urges trigger 34 to its rest position while maintaining contact with the ratchet element 38.

Successive pumps on the trigger 34 to move the trigger upwards in FIG. 1, against the bias of leaf spring 46, cause successive corresponding passes of the ratchet element 38 across the rotational axis 42 of the take-up reel shaft 32, causing the shaft 32 to rotate clockwise, as shown in FIG. 1. Movement of the trigger 34 upwards cause distal end 47 of leaf spring 46 to slide along the surface of ratchet means 38, never losing contact therewith. Thus, a force constantly applied on the ratchet element 38 by the leaf spring 46 urges ratchet element into engagement with the toothed gear 35, so that controlled proximal withdrawal of outer tube 16 if achieved without the risk of no-load operation of the trigger 34. Note how the end 47 of leaf spring 46 remote from its mounting point 48 urges the ratchet element 38 into contact with windlass gear wheel 35, but nevertheless allows the ratchet element 38 to return to its start position with the downward movement of the trigger 34. The trigger 34 and ratchet element 38 are helped to return to their original dispositions by the bias spring 46 acting on the trigger 34. Helical spring portion 56 of leaf spring 46 rests on the interior surface of trigger 34, as shown in FIG. 1.

FIG. 1 also shows pivot axis of trigger 34 at pivot point 41. By pushing trigger upwards, trigger slightly rotates around axis 41, thereby moving ratchet element 38 connected with trigger 34 at mounting point 40 upwards and causing windlass gear 35 to rotate clockwise. This clockwise rotation of windlass gear 35 causes pulling on line 30 moving hub 18 and therewith outer tube 16 proximally, resulting in deployment of the stent at the distal end of the coaxial stent delivery device.

A pawl 44 is mounted to the housing 12, and engages successive teeth of the take-up gear 35, to prevent any anticlockwise return movement of the reel 32 as the ratchet element 38 returns to its initial position.

However, pumps on the trigger 34 are not the only way to bring the slider 24 proximally along the rails 22. As mentioned earlier, one can manually grip the slider 24 and urge it proximally along the rails 22, without any contact at all with the trigger 34. In this case, either the pull wire 30 becomes loose and meanders within the housing 12 (that is to say, it collapses), or else, by the provision of a suitable wind-up mechanism or spring (not shown) on the take-up reel 32, any relief of tension in the wire 30 is met with a corresponding clockwise rotation of the reel 32, to take up any slack in the wire 30. Either way, the person delivering the stent has the option of pumping on the trigger 34, or pulling on the slider 24.

The hub 18 is provided with a fluid inlet port 50 in the form of a luer lock. This is useful for injecting radiopaque fluid into the bodily lumen which is to be stented for the reason explained above. The luer lock, modified accordingly, is also used to fix the axial position of outer tube 16 in the event the medical practitioner needs to interrupt the release operation of the stent.

Figure 2:
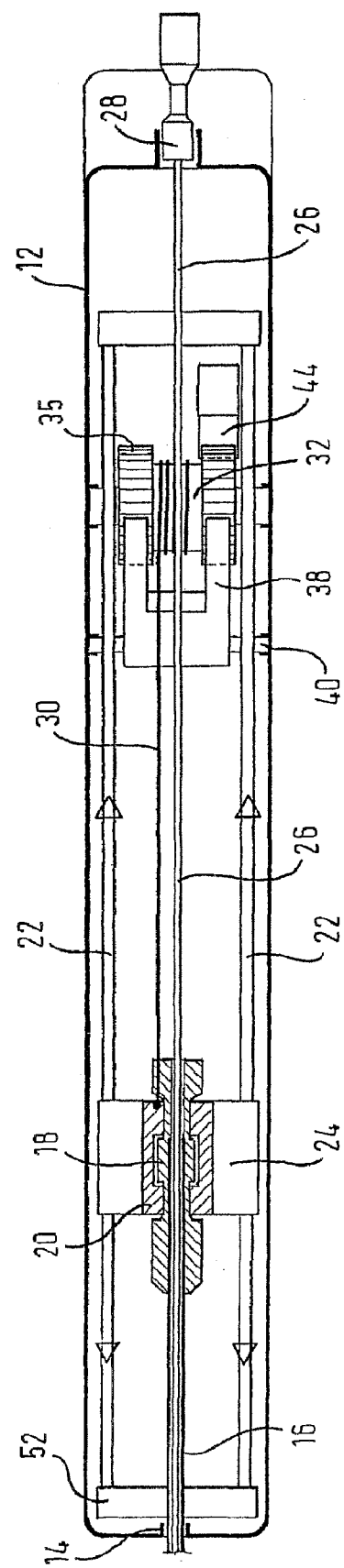
FIG. 2 is a schematic representation, seen from above, of the core components of the FIG. 1 device, enabling the interaction of the different components to be appreciated further.

FIG. 2 is a schematic representation in plan of the device shown in FIG. 1. FIG. 2 shows how line 30 is wound around the windlass gear shaft 32. The winding of line 30 may be achieved by a spring-biased (not shown) reel which reels in any slack in line 30 automatically upon proximal movement of slider 24. According to FIG. 2, the shaft 32 can be formed as a drum flanked at each end by a gear wheel 35, each wheel having its own ratchet element 38, both pivotally mounted to the trigger 34. This assists management of the reeling in of the pull wire 30.

The above description is of a device to fit at the proximal end of a coaxial catheter device for percutaneous transluminal stent delivery. In such systems, it is customary to provide a hub at the proximal end of the two coaxial elements of the system. What is contemplated is that the present device will engage with these two hubs, and allow the usual range of connections to be made to each of the hubs. Thus, for example, it is to be expected that a guide wire will extend proximally from the hub at the proximal end of the inner element of the coaxial system, that the hub of the outer sheath will seal with the inner coaxial element and that it will also have a port arrangement for the admission or withdrawal of liquids from the annular space between the two coaxial elements of the system.

It is the intention that the above described system should have wide application to different stent delivery systems, this being facilitated by provision of easily exchangeable engagement formations in the housing for the respective hubs.

For ease of use, it is contemplated that the housing would display identical left and right sides, a lower edge with the trigger in it, and an upper edge in which the track for receipt of the coaxial stent delivery element is open-topped, so that the stent delivery system can be laid into a recess in the top edge of the housing which extends all the way from one end of the housing to the other. Those skilled in this art will be able to envisage other arrangements.

By providing the trigger 34 with different bores, to mount it on the housing at several different locations relative to the ratchet element 38, a choice of different strokes can be offered, to achieve a desired length of withdrawal of outer sleeve 16 for each stroke of the trigger.

The formation which receive hubs 18 and 28 can be made in the form of resilient clips, so that a variety of different delivery systems can be laid into the track 14.

In fact, the device is designed with flexibility in mind, to enable its use with a range of delivery devices and a range of user characteristics. The housing is deliberately designed symmetrical, that is, not "handed", so it is equally suitable for left-handed and right-handed use.

A stopper may be provided on rails 22 as an indicator or reminder for the medical practitioner that a certain stent length has been deployed and to continue the deployment procedure by manually moving the slider 24 proximally on the rails 22. The stopper may be removed or it may be in the form of a discontinuity on the surface of the rails 22, offering a resistance to slider travel that may easily be overcome manually when continuing the deployment procedure by moving the slider 24 proximally. This provides tactile feedback to the surgeon giving him/her assurance that the stent has been fully deployed.

The materials used for the manufacture of the stent delivery device are, but not limited to, polyoxymethylene (POM), polycarbonate (PC) and other polymer compositions conventionally used for molding medical devices. Other components, such as the rails and the leaf spring, are made from metal suitable for medical instruments, such as stainless steel with designation 1.4310 or 1.4301. Other materials will be known and readily available to those skilled in the art.

Line 30 is a multifilament polymer-based fiber which gives line 30 greater flexibility than a monofilament line is likely to deliver. This flexibility is important when slider is moved proximally releasing tension in the line which then meanders within the housing.

Figure 3:
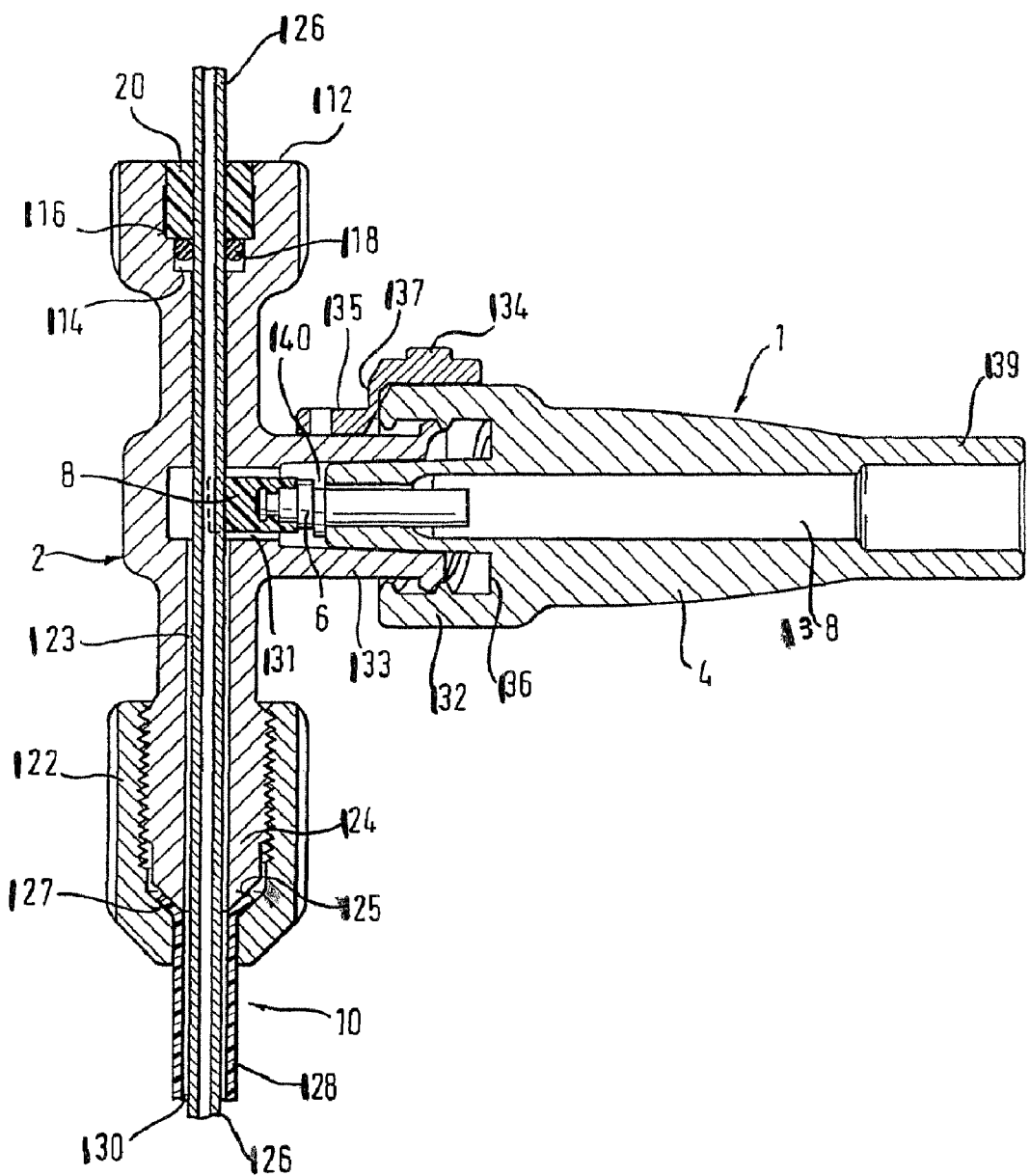
FIG. 3 shows in cross-section a device having a locking and release device attached thereto.

FIG. 3 shows a cross-sectional view of a device for passing fluid into an annular cavity 130 of a housing of the device (which takes the form of a T-piece 2) and also between an inner catheter 126 and an outer sleeve 128.

The device has a housing in the shape of a T-piece 2 comprising a distal end 124, a proximal end 112 and an off-axis end 136. A lumen 123 extends between the proximal and distal ends, and is in fluid communication with a lumen 131 in the side branch of the T-piece which leads to the off-axis end 136. It is the distal 124 and the proximal 112 which define the axis of the device. The outer sleeve 128 of a stent delivery system is attached to the threaded distal end 124 of the device via a threaded female collar 122. The female collar 122 comprises a central through-hole through which the outer sleeve 128 is inserted and thermally clamped to the female collar 122. By "thermal clamping" is meant that the material of the proximal end of the outer sleeve 128 expands upon thermo-forming heat treatment and retains its expanded shape when it returns back to ambient temperature. Hence, the radially-expanded proximal end of the outer sleeve 128 resists distal movement of the outer sleeve relative to the collar 122 when the process of thermal treatment is completed. It is also conceivable to use other means to attach the outer sleeve 128 to the distal end of the device, such as a press-fitting using re-entrant surfaces, or suitable adhesives. A seating 125 of the housing seals with a complementary seating 127 of the threaded collar 122.

The proximal end 112 of the device, as shown in FIG. 3 exhibits a recess having two different diameters whereby the innermost recess 114 in an axial direction accommodates an O-ring 118 for providing a fluid-tight seal with an inner catheter 126 and a plug 120 press-fitted into the larger diameter recess 116 in order to prevent the O-ring from slipping out of the smaller recess upon proximal movement of the inner catheter 126. It is also conceivable to screw the plug into the larger diameter recess or use an appropriate adhesive. Differently sized O-rings can be used to accommodate differently sized inner catheters for differently sized stents. This further enhances the versatility of the device.

The off-axis end 36 of the device shows a female luer-lock element 133 which connects to a male luer-lock assembly 132 thereby to serve as the locking and release device 11. Thus, the locking and release device 11 may also be recognized to be based on a luer-lock connector. It comprises a passage 138 therethrough for passing fluid down the inner bore of the luer connector. The inner end of the male luer connector 132, which extends into the off-axis end of the T-piece 2, comprises a spigot 6 which is coaxial with, and located within, the internal bore 138 of the luer connector. The spigot 6 is fixed inside the bore 138 of the luer connector. The spigot 6 is fixed inside the bore 138 of the luer connector by means of an annular cutting edge which cuts itself into the material of the luer connector (in the manner of a self-tapping screw) and thereby fixedly fastens the spigot 6 to the luer connector 1. It is also conceivable to screw or press-fit the spigot into the luer connector. The spigot 6 comprises a cut-out portion 140 at the end extending into the T-piece for providing a continuous passage for the fluid to be injected that is to say, fluid communication between the bore 138 and the lumen 123. The lower (in FIG. 3) end of the spigot 6 comprises a re-entrant surfaces onto which an elastically deformable elongate locking member 8 is attached. The locking member 8 is made out of silicone rubber but other materials can be used. The end surface of the locking member 8, remote from the spigot 6, constitutes a pressure pad which bears on the inner catheter 126 when the locking member is in its locking disposition, as explained below.

A distinct feature of the luer connector is its quick and easy installation, since it requires only less than half a turn to fully engage the male luer-lock connector 132 with the female portion 133 of the mating luer-lock on the off-axis side branch of the T-piece. The dimensions of the spigot 6 and the pressure pad 8 are such that, when bringing the male luer-lock connector 132 into full engagement with the female element 133, the deformable locking member 8 extends sufficiently far enough beyond the end of the luer-lock connector so that it experiences a compressive force due to pressing down onto the inner catheter 126. This means that, in the absence of the inner catheter 126, the elastic member intersects the locus or line of presence of the inner catheter, so that it undergoes deformation when such inner body is present. It is this compression of the locking member which prevents axial sliding movement of the inner catheter within the device. In this locking disposition, fluid can still be injected through the luer-lock connector down into the T-piece lumen 123 and thereafter the annular cavity 130 between the inner catheter 126 and the outer sleeve 128. For ease of use, a syringe can easily be attached to the upper end 139 of the male luer-lock element 132, that is, the end opposite the one being connected to the T-piece of the luer connector via a luer-lock connection, which upper ends 139 for this purpose can exhibit the characteristic cone angle of a female luer-lock portion.

The luer connector optionally comprises a safety catch which prevents inadvertent release of the male luer connector 132 from the T-piece 2. The safety catch illustrated comprises two portions, namely a portion 134 located on the male luer connector 132 and preferably glued thereon and a portion 135 on the female luer portion 133 and preferably glued to it. Between the portions 134, 135 is a frangible neck 137, which prevents rotation of the luer connector until it is broken by relative rotation of the male and female luer-lock portions. To release the safety catch, the luer connector is rotated counterclockwise thereby breaking the frangible neck 137. The safety catch is conveniently made of polymeric material. It is also conceivable to bring a pawl into engagement with a spring-biased toothed annulus on the housing 2 close to the off-axis end of the T-piece. To disengage the safety catch, the spring-biased toothed annulus is pushed towards the T-piece, thereby releasing the pawl and disengaging the luer connector. Also, a shear pin for blocking the rotation of the luer connector until it is broken in shear, or any other conventional locking mechanism that is suitable in size and weight can be used.

The entire structure is conveniently made out of synthetic polymeric materials.

Figure 4:
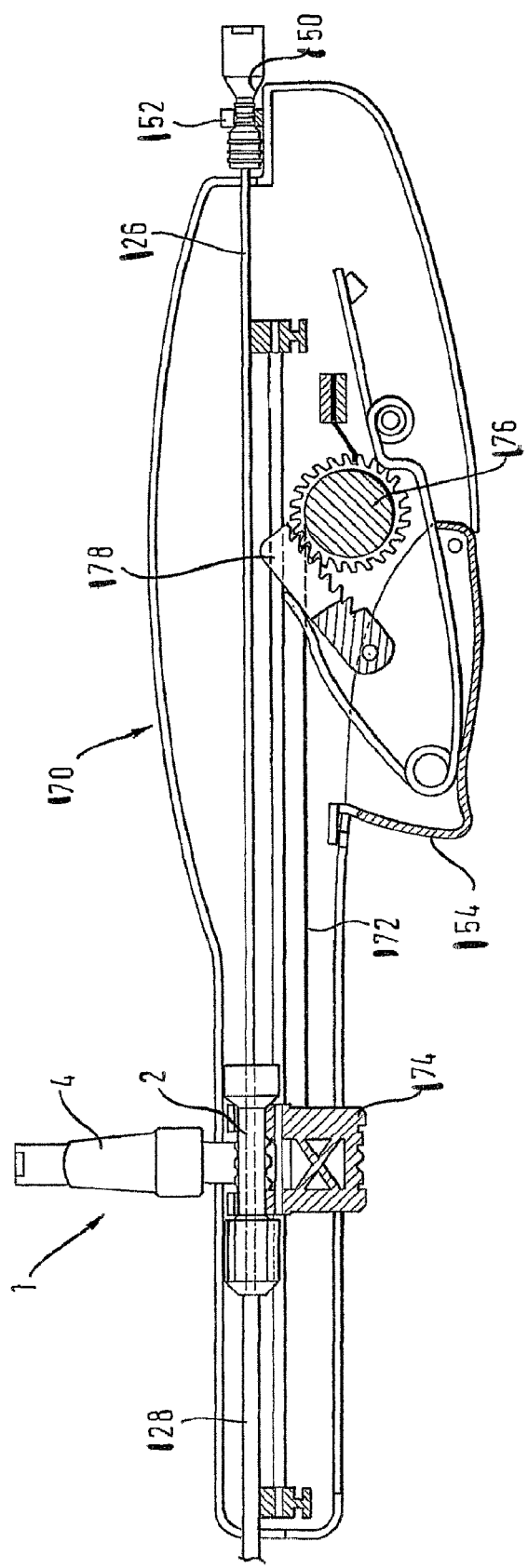
FIG. 4 is a longitudinal section through a stent delivery system using the locking and release device of FIG. 3.

FIG. 4 shows a perspective view of the stent delivery system as described in connection with FIGS. 1 and 2 using the locking and release device as well as the T-piece of FIG. 3 in an assembled state. The delivery system 170 is based on a trigger-principle for the proximal withdrawal of the outer sleeve with respect to the inner catheter. The proximal and distal end of the T-piece connector are engaged with mating parts of the delivery system, whereby the proximal ends 150 of the inner catheter 126 is fixed in position by a mount 152 at the rear side of the trigger device. Upon actuation of the delivery system the T-piece is drawn rearwardly by a tension wire 172 and carriage 174, with successive squeezes of a trigger 154, that reel in the wire 172 on a capstan drum 176 which the trigger rotates through a rack 178. The carriage 174 carries the luer-lock housing 2 towards the rear mount 152 step-wise, with each squeeze of the trigger 154, and thereby withdraws the outer sheath 128 to gradually release the stent.

During insertion of the stent into the delivery system, sterilization and transport, the luer-lock connector remains in its locking disposition, thereby preventing inadvertent sliding movement of the inner catheter with respect to the outer sleeve. It is only shortly before deploying the stent into the body lumen, that the luer-lock connector 1 is disengaged from the T-piece 2. Once the stent has been properly placed at the site of the stenosis, the surgeon uses the trigger mechanism in order to proximally withdraw the outer sleeve and to release the stent. In case the surgeon has to temporarily interrupt the procedure of stent placement, the luer-lock connector can be inserted back into the T-piece in order to fix the position of the inner catheter with respect to the outer sleeve.

Figure 5:
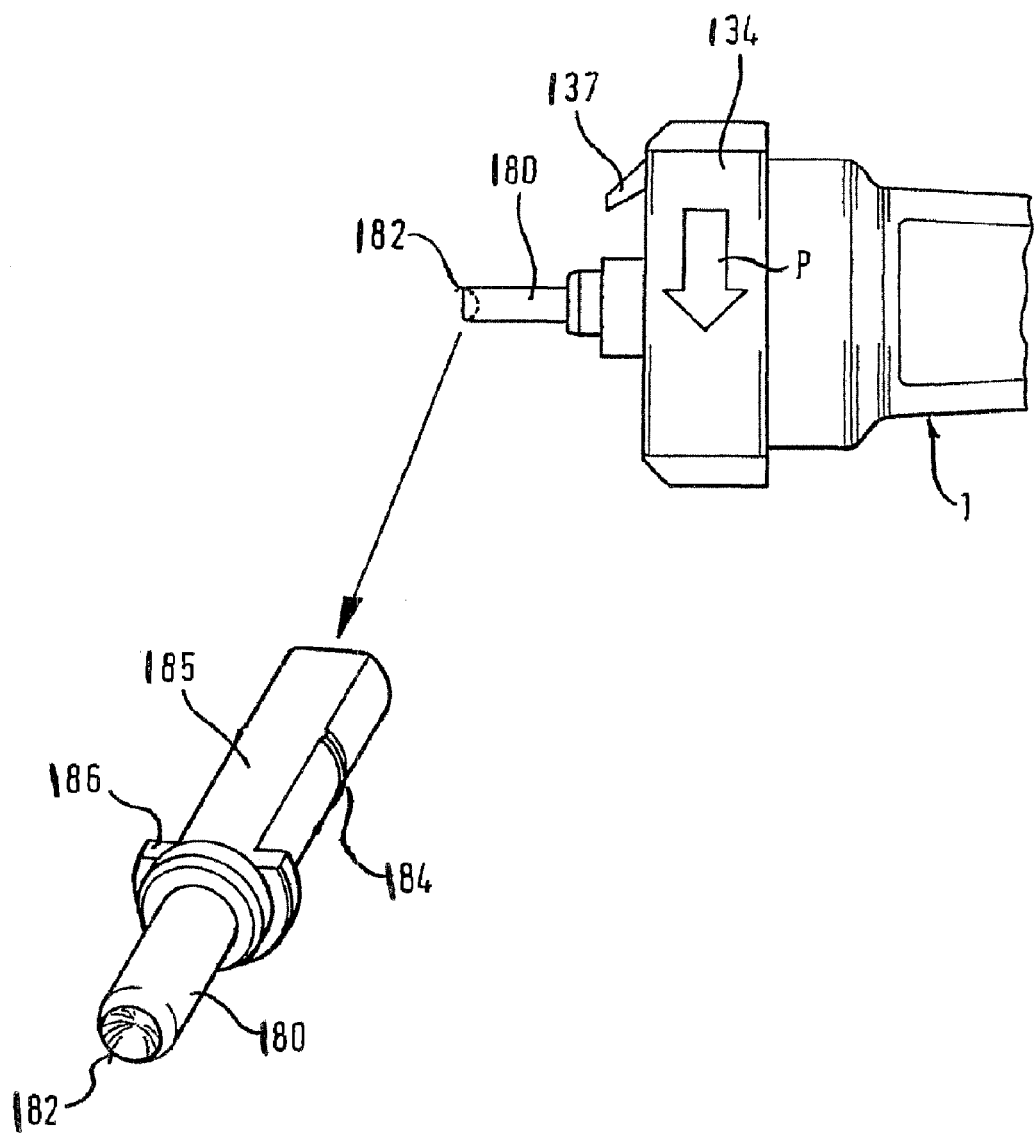
FIG. 5 shows in cross-section another embodiment of the locking and release device.

FIG. 5 shows in cross-section another embodiment of the locking and release device 1 in FIG. 3. It connects to the female luer-lock element 133 at the off-axis end 136 of the device shown in FIG. 1 and comprises a passage therethrough (not shown) for passing fluid down the inner bore of the luer connector 1, into lumen 123 of the T-piece connector 2.

The inner end of the locking and release device 1 which extends into the off-axis end of the T-piece 2 comprises a metal pin 180 which is coaxial with, and located within, the internal bore (not shown) of the luer connector. The metal pin 180 is fixed inside the bore of the luer connector by means of a press-fit. The end of the metal pin extending into the off-axis end of the T-piece is domed. The end surface of metal pin curves radially inwardly, uniformly from all radial directions. This dome-shape of the axial end of metal pin 180 effects line contact the annular edge 182 of metal pin 180 with the inner catheter 126. The dome-shaped end of metal pin 180 is also more clearly shown in the blown-up part of FIG. 5.

For providing fluid communication between the inner bore of the luer connector 1 and lumen 123 of T-piece 2, the upper portion of metal pin in FIG. 5 to be inserted into the off-axis end of T-piece is oblate. When the metal pin is inserted into the male Luer connector, a gap remains between the oblated portion 185 of metal pin and the end portion of the luer connector defining the inner bore. This way, fluid connection between inner bore 138 of luer connector 1 and inner lumen 123 of T-piece is established.

The press-fit of metal pin into male luer connector is ensured by the chamfered portion 184 of metal pin. A flange 186 serving as a stopper is provided on the metal pin. The flange also takes up any compressive stresses caused by the pushing of the pin onto the inner catheter.

To prevent inadvertent rotation of the male luer-lock connector 1 with respect to the T-piece, an integrally molded element is both attached to the luer connector and the off-axis end of the T-piece. This element comprises portion 134, which circumferentially surrounds the near end of the luer connector to the off-axis end of the T-piece, a frangible portion 137 and portion 135 circumferentially surrounding a section of the off-axis end of the T-piece. Arrows are provided on portion 134 indicating the medical practitioner what direction to turn the luer connector in order to release it from the T-piece.

Upon rotation of the luer male connector 1, frangible portion 137 breaks off portion 135, thereby allowing the luer connector to be detached from the T-piece. The frangible portion 137 is designed such that it resists inadvertent rotation of the luer connector prior to use of the luer connector/T-piece assembly. It also serves as an indicator for the surgeon to indicate that the device shown in FIG. 3 has not been previously used in a surgical procedure, and sterility is still maintained.

The circular edge 182 of dome-shaped end of metal pin 180, in an assembled state of the device shown in FIG. 1, bites on the inner catheter 126 and prevents distal or proximal movement of the inner catheter with respect to the T-piece. The inventor of the present application have found that it is the sharp edge of metal pin 180 that effectively prevents this movement of the inner catheter. Preferably, the diameter of the 360° circular edge equals the diameter of the inner catheter 126. It is also contemplated that the material used for the metal pin should be harder than the material used for the inner catheter.

Although the illustrated embodiment shows a single T-piece being used for both introduction of radiopaque marker fluid and for clamping the inner catheter relative to the outer sheath, and although this is a useful advantage of the invention, nevertheless, it will be appreciated that separate T-pieces could be used for these two separate functions. The advantage delivered by this invention, namely reliable and economical inner catheter clamping remains, even if radiopaque fluid is delivered elsewhere.

The invention claimed is:
1. A stent delivery system, comprising:
a hub coupled to an outer tube;
a slider coupled to the hub, the slider disposed over a track fixed to a housing, the track comprising a pair of parallel rails, the slider having a first position corresponding to a distal position of the outer tube constraining a stent, and a second position corresponding to a proximal position of the outer tube releasing the stent, the slider having a portion protruding outside of the housing enabling manual movement of the slider to the second position; a pull wire having a first end attached to the slider and a second end coupled to a take-up reel; and a trigger biased to a rest position by a leaf spring mounted to the housing, wherein actuation of the trigger incrementally moves the slider along the track.

2. The stent delivery system according to claim 1, wherein the take-up reel carries a gear having teeth that engage with complementary teeth on a ratchet element that is mounted to the trigger.

3. The stent delivery system according to claim 2, further comprising a pawl mounted to the housing engaging the gear teeth to prevent movement of the gear when the trigger returns to its rest position following actuation.

4. The stent delivery system according to claim 1, wherein the track is an integral part of the housing.

* * * * *